United States Patent [19]

Zuckerman

[11] Patent Number: 5,186,173
[45] Date of Patent: Feb. 16, 1993

[54] METHOD FOR IN VIVO MEASUREMENT OF OXYGEN CONCENTRATION LEVELS

[75] Inventor: Ralph Zuckerman, Philadelphia, Pa.

[73] Assignee: Drexel University, Philadelphia, Pa.

[21] Appl. No.: 567,486

[22] Filed: Aug. 14, 1990

[51] Int. Cl.⁵ .............................................. A61B 5/00
[52] U.S. Cl. ................................ 128/633; 128/666; 351/221; 351/205
[58] Field of Search ................ 128/633–644, 128/664–666; 351/221, 205–207; 354/62

[56] References Cited

U.S. PATENT DOCUMENTS

| | | |
|---|---|---|
| Re. 31,879 | 5/1985 | Lübbers et al. |
| 3,893,447 | 7/1975 | Hochheimer et al. |
| 3,915,564 | 10/1975 | Urban |
| 4,003,707 | 1/1977 | Lübbers et al. |
| 4,041,932 | 8/1977 | Fostick |
| 4,166,695 | 9/1979 | Hill et al. |
| 4,213,678 | 7/1980 | Pomerantzeff et al. |
| 4,215,940 | 8/1980 | Lübbers et al. |
| 4,249,825 | 2/1981 | Shapiro |
| 4,269,516 | 5/1981 | Lübbers et al. |
| 4,304,720 | 12/1981 | Dean et al. |
| 4,341,223 | 7/1982 | Lutz |
| 4,350,676 | 9/1982 | Laties et al. |
| 4,412,543 | 1/1983 | Vassiliadis et al. ........... 128/633 |
| 4,423,931 | 1/1984 | Shapiro |
| 4,476,870 | 10/1984 | Peterson et al. |
| 4,579,430 | 4/1986 | Bille |
| 4,580,059 | 4/1986 | Wolfbeis et al. |
| 4,753,958 | 6/1988 | Weinstein et al. ........... 514/410 |
| 4,810,655 | 3/1989 | Khalil et al. ................. 128/633 |
| 4,861,727 | 8/1989 | Hauenstein et al. |
| 4,891,043 | 1/1990 | Zeimer et al. ................ 604/20 |
| 4,947,856 | 8/1990 | Vanderkooi et al. .......... 128/665 |

OTHER PUBLICATIONS

Vanderkooi, J., et al., "An Optical Method for Measurement of Dioxygen Concentration Based Upon Quenching of Phosphorescence," *J. Biol. Chem.*, 262(12):5476–82 (Apr. 25, 1987).
*Dorland's Illustrated Medical Dictionary* (26th ed. 1981), p. 380.
Vaughan, W. M. et al., "Oxygen Quenching of Pyrenebutyric Acid Fluorescence in Water. A Dynamic Probe of the Microenvironment", *Biochemistry*, 9(3):464–73 (1970).

*Primary Examiner*—Kyle L. Howell
*Assistant Examiner*—Robert L. Nasser, Jr.
*Attorney, Agent, or Firm*—Panitch Schwarze Jacobs & Nadel

[57] ABSTRACT

A method for in vivo measurement of oxygen concentration levels in animal bodily fluids or tissues comprises administering a biocompatible fluoroescent probe sensitive to oxygen quenching and having a known unquenched fluorescence intensity to an animal body in an amount sufficient to allow the probe to accumulate in the fluid or tissue, exposing the fluid or tissue to excitation light, measuring fluorescent emission light intensity from the probe in the fluid or tissue and determining the oxygen concentration level of the fluid or tissue by comparing the known unquenched fluorescence intensity and the measured fluorescence intensity. This method preferably uses a biocompatible fluorescent probe comprising pyrenebutyric acid or its biocompatible salt form.

21 Claims, 4 Drawing Sheets

METHOD FOR IN VIVO MEASUREMENT OF OXYGEN CONCENTRATION LEVELS

STATEMENT OF GOVERNMENT INTEREST

This invention was made, in part, with Government support awarded by the National Institutes of Health.

FIELD OF THE INVENTION

The present invention relates to a method for in vivo measurement of oxygen concentration levels in animal bodily fluids or tissues and, more particularly, in vivo measurement of oxygen concentration levels using an injectable, biocompatible fluorescent probe which accumulates in animal bodily fluids or tissues.

BACKGROUND OF THE INVENTION

It is known in the medical and biological arts that oxygen is a necessary component of animal metabolism. An oxygen supply is especially important in those bodily tissues undergoing continuous and critical activity, such as cardiac muscle, brain tissue and other nerve tissue. One example highlighting the desirability of having a method to determine oxygen concentration levels in animal tissues is diseases of the retina.

Retinal vascular disease is one of the leading causes of blindness in the United States and the major cause of vision loss throughout the world. Subtle changes in retinal tissue oxygenation, most notably tissue hypoxia, have been implicated as causal factors in the etiology of neovascularization in diabetic retinopathy, neovascularization following branch vein occlusion, sickle-cell anemia retinopathy, retrolental fibroplasia (retinopathy of prematurity), and hypertensive changes in the retinal vasculature, to name a few.

Despite the dominant role of retinal oxygen concentration in retinal vascular disease, no method exists for the diagnosis of oxygen concentration levels within the tissue of the retina in vivo. In addition, there are no methods for evaluating the benefits of treatment modalities to retinal oxygenation in retinal disease, such as panretinal photocoagulation. Moreover, because retinal tissue hypoxia is believed to precede changes in the retinal vasculature, it would be desirable to determine the retinal tissue oxygen concentration levels to allow early diagnosis of disease and treatment intervention prior to irreversible changes in the retinal tissue and vessels.

Because oxygen is generally transported to the retina and other various tissues in the body by the circulatory system, many tests or analyses for oxygen content in bodily tissues are conventionally directed to detecting the presence and/or viability of blood vessels in and around particular tissues in the body and blood flow within these vessels. Fluorescein angiography is one popularly used technique to determine the presence of blood vessels and blood flow in vivo as described, for example, in U.S. Pat. No. 3,893,447 of Hochheimer et al.; U.S. Pat. No. 4,249,825 of Shapiro; U.S. Pat. No. 4,304,720 of Dean et al.; and U.S. Pat. No. 4,341,223 of Lutz. However, these methods and apparatus are limited to the analysis of the blood vessels which is, at best, only an indirect approximation of the oxygen concentration levels in surrounding tissue.

Fluorescein angiography and similar fluorescence techniques are based on the knowledge that certain dyes are known to have the ability to fluoresce. The fluorescence of such dyes may be reduced by the addition reaction of certain substances, commonly called quenchers, to or with the dye. Fluorescent dyes having a known sensitivity to a particular quencher may be used as an indicator for the concentration of that particular quencher. When illuminated by a source beam of excitation light of a predetermined wavelength, the indicating dye typically emits a fluorescent beam of a wavelength different from the source beam and whose intensity is inversely proportional to the concentration of the particular quencher.

The relation between the concentration of the quencher and the reduction in fluorescence intensity is known generally as the Stern-Volmer relation which may be expressed as follows:

$$F_o/F = 1 + k[Q]$$

where $F_o$ is the fluorescence intensity of a fluorescent indicator in the absence of a quencher, F is the fluorescence intensity of a fluorescent indicator in the presence of a quencher, k is the quenching constant specific to each pair of quencher/fluorescence indicator and [Q] is the concentration or partial pressure of the quencher.

Several fluorescent dyes sensitive to oxygen quenching are known, and their uses have been described by U.S. Pat. No. 4,041,932 of Fostick; U.S. Pat. No. 4,476,870 of Peterson et al.; U.S. Pat. No. 4,580,059 of Wolfbeis et al.; and U.S. Pat. No. 4,861,727 of Hauenstein et al.; and W. M. Vaughan et al. "Oxygen Quenching of Pyrenebutyric Acid Fluorescence in Water. A Dynamic Probe of the Microenvironment," *Biochemistry*, 9(3):464-73 (1970), for example. These methods of measuring oxygen concentration using fluorescent indicators are, however, limited to in vitro measurements of oxygen concentration levels or in vivo application for fluids only. Moreover, those in vivo methods for measuring fluids, principally blood, require the use of implantable or insertable sampling chambers through which the fluid or its constituents may be viewed or collected for analysis. No fluorescent indicator is present in the body fluid but, rather, is contained in the sampling chamber. In addition, these in vivo methods provide no direct measurement of oxygen concentration levels in bodily tissues.

In the view of the deficiencies of the prior art, it would be desirable to have a method for direct in vivo measurement of oxygen concentration levels in bodily fluids or tissues.

BRIEF SUMMARY OF THE INVENTION

According to the present invention, a method for in vivo measurement of oxygen concentration levels in animal bodily fluids or tissues comprises injecting a biocompatible fluorescent probe sensitive to oxygen quenching and having a known unquenched fluorescence intensity into the animal body in an amount sufficient to allow the probe to accumulate in the fluid or tissue, exposing the fluid or tissue to excitation light, measuring the fluorescent emission light intensity from the probe in the fluid or tissue and determining the oxygen concentration level of the fluid or tissue by comparing the known unquenched fluorescence intensity and the measured fluorescence intensity.

The method is preferably performed using intravenous or intraperitoneal injection of the probe in a suitable solution and using ultraviolet citation light.

DETAILED DESCRIPTION OF PREFERRED EMBODIMENTS

Figure 1:
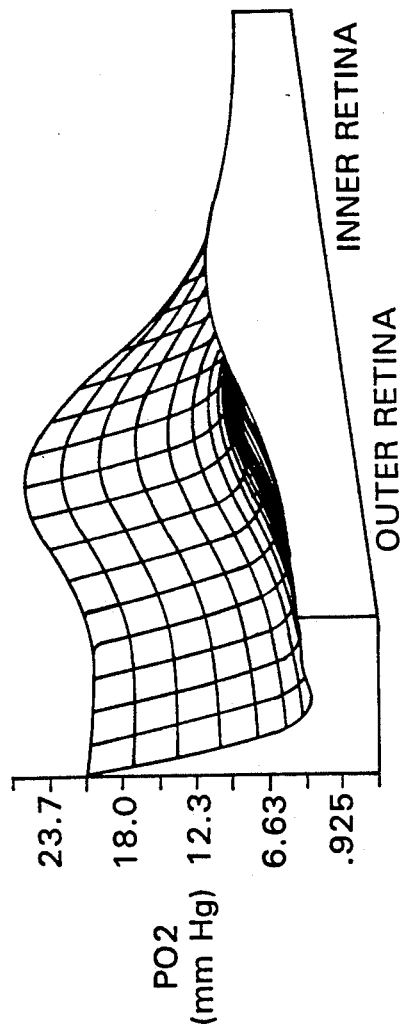
FIG. 1 is a graphical surface plot of the steady state $PO_2$ values along and within the retinal layers of a frog retina, obtained with an oxygen microcathode.
Figure 2:
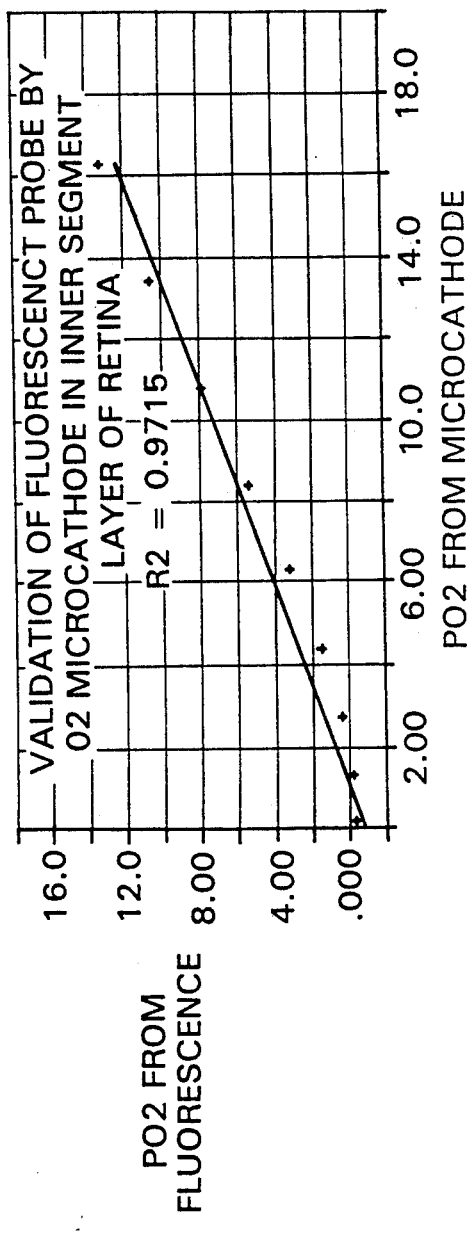
FIG. 2 is a graphical comparison of the $PO_2$ obtained with an oxygen microcathode as shown in FIG. 1 with the $PO_2$ values derived from a fluorescent probe of the invention.

Although the method for in vivo measurement of oxygen concentration levels applies to measuring such levels in animal bodily fluids or tissues generally, a method is described and exemplified below with specific examples wherein the method of the present invention is used to measure oxygen concentration levels in the retina. It would be readily appreciated by one skilled in the art in view of this disclosure, however, that other bodily fluids and tissues may be measured for oxygen concentration levels using the method of the present invention.

According to the present invention, a method for in vivo measurement of oxygen concentration levels in an animal bodily fluid or tissue comprises the use of a biocompatible fluorescent probe which is sensitive to oxygen quenching. Several fluorescent probes sensitive to oxygen quenching and their intensities in an unquenched state are known. However, many of these fluorescent indicators or probes have relatively short fluorescent lifetimes on the order of about 10 to 20 nsec. While oxygen is known to be a powerful quencher of electronic excited states, its influence upon such short lifetime fluorescence is negligible. Moreover, because the partial pressure of oxygen ($PO_2$) in animal bodily fluids and tissues typically ranges from about 0 to 700 mm Hg, it is preferred to have a fluorescent probe sensitive to oxygen quenching which has a fluorescent lifetime sufficient to allow enough time for oxygen molecules to impinge on and thereby quench the effective fluorescence decay and which exhibits a long enough period of decay so that the quenching effect may be quantified to effectively distinguish between physiologic $PO_2$ values.

Preferably according to the present invention, the fluorescent probe has a fluorescent lifetime greater than about 70 nsec and a fluorescent lifetime of about 135 nsec is presently preferred. Further, the fluorescent probe must be biocompatible, causing the least amount of damage to fluid and tissue and causing relatively few, if any, untoward side effects. Suitable examples of the fluorescent probe include pyrenebutyric acid or its biocompatible salt form. Pyrenebutyric acid possesses a relatively long fluorescence lifetime of about 135 nsec and is powerfully quenched by oxygen concentrations that fall within the physiologic range typically found in animal bodily fluids and tissues. It is presently preferred that the fluorescent probe comprises sodium pyrenebutyrate, although one skilled in the medical and biological arts will appreciate that other salt forms of pyrenebutyric acid may be used in accordance with the present invention as well as other biocompatible fluorescent probes having the desired characteristics described above.

To facilitate administration to the animal body, it is presently preferred that the fluorescent probe is present in a non-toxic solution, such as dimethyl sulfoxide (DMSO) or physiologic saline, although other vehicles and carriers may be used in accordance with the present invention, depending on the solubility characteristics of the fluorescent probe and the type of bodily fluid or tissue to be examined, among other factors.

The fluorescent probe is preferably present in the solution in an amount of about 50 mg to about 1000 mg per ml of solution depending on the solubility of the probe in the solution. In one example, where the fluorescent probe comprises sodium pyrenebutyrate and the non-toxic solution comprises DMSO, the fluorescent probe is present in the solution in an amount of about 250 mg per ml of solution, although one skilled in the art will appreciate that higher and lower fluorescent probe concentrations may be used.

While it is possible to inject the fluorescent probe locally into the fluid or tissue to be examined, it is presently preferred to use the simpler and more systemic method of intravenous or intraperitoneal injection. According to the present invention, the fluorescent probe is injected into the animal body in an amount sufficient to allow the probe to accumulate in the fluid or tissue to be examined. The level of fluorescent probe accumulation desired may depend, in part, on the ability or sensitivity of the measuring means (discussed below) to measure the fluorescence emission from the probe in the fluid or tissue. The level of accumulation in a particular tissue or fluid is dependent on, among other factors, the dosage administered in accordance with the present invention. For example, where it is desired to examine the oxygen concentration levels in retinal tissue in accordance with the present invention, the fluorescent probe is present in a non-toxic solution and is preferably administered in an amount of about 25 mg to about 250 mg of the probe per kg of body weight and, more preferably, about 150 mg per kg of body weight, although one skilled in the art will understand in view of this disclosure that higher and lower dosages may be used.

In an alternative embodiment of the present invention where it may be desired to avoid systemic injection of the fluorescent probe, the probe may be administered topically, such as to the cornea and other epithelial tissues. In still another embodiment of the present invention, the probe is administered using means for targeting the probe to a predetermined tissue type in the animal body.

One example of such targeting means is the use of a liposome to form a membrane around and encapsulate the fluorescent probe for injection into the animal body. The liposome preferably comprises a lipid type exhibiting a specific affinity for the bodily fluid or tissue to be targeted. For example, retinal-based liposomes are light sensitive and release their contents when stimulated by light. Such a liposome may be used in accordance with the present invention to target the fluorescent probe contained in the liposome to the eye, for example, where light entering the eye would cause release of the probe while substantially avoiding release of the probe in other areas of the body not subjected to light.

Once the fluorescent probe has been administered into the animal body, the fluorescent probe is allowed to accumulate in the bodily fluid or tissue desired to be examined. While not intending to be bound by any particular theory, I believe that pyrenebutyric acid or its biocompatible salt form accumulates within membrane structures due to the hydrophobic nature of the pyrene ring. In addition, the pyrenebutyric acid or its salt form binds to proteins. Thus, given time, the fluorescent probe of the present invention accumulates in the tissues and fluids of the animal being studied. For example, where it is desired to measure the oxygen concentration level in retinal tissue, the time necessary to allow the fluorescent probe to accumulate in the retinal tissue is generally about one hour. The time necessary to allow the probe to accumulate in other bodily fluids or tissues may vary, depending on the type and density of the fluid or tissue and its accessibility from the site of probe injection.

With the fluorescent probe present in the bodily fluid or tissue, the fluid or tissue is then exposed to excitation light to cause the probe to fluoresce. It is believed that the method of the present invention may be applied to virtually any bodily fluid or tissue accessible to excitation light means and measuring means (discussed below). For example, where the tissue to be measured comprises retinal tissue, excitation light and measuring means may be operated from outside the body through the relatively clear components of the eye. Other bodily fluids and tissue may be examined using commercially available fiber optic devices along which excitation and emission lights may be transmitted and received, for example.

The excitation light should comprise wavelengths sufficient to cause an excited state in the fluorescent probe, the decay of which produces fluorescent emission light. Preferably, the excitation light may be produced by excitation means, such as a mercury lamp or xenon strobe equipped with a suitable excitation filter, capable of producing ultraviolet light. Where the fluorescent probe comprises pyrenebutyric acid or its biocompatible salt form, the excitation light preferably has a wavelength of about 340 nm with a 25 nm bandpass.

The fluorescence emitted by the fluorescent probe in the bodily tissue or fluid in response to the excitation light generally has wavelengths greater than about 400 nm where the fluorescent probe comprises pyrenebutyric acid or its biocompatible salt form. This emission light may be isolated from any reflecting excitation light using, for example, an emission filter which passes emission light wavelengths greater than about 400 nm to measuring means.

The measuring means should be capable of measuring the relative intensities of the light emitted from the fluorescent probe in the bodily fluid or tissue. One example of suitable measuring means comprises a commercially available optical detector comprising a high-gain, low-noise charged coupled device (CCD) camera such as the COHU Model 4815 CCD camera, the DAGE Intensified CCD camera Model 72I or the Photometrics Ltd. Star One Chilled CCD camera, although other devices, such as a modified fundus camera, silcon-intensifier-target tube cameras (SIT), photodiode arrays and photomultipliers may be used in accordance with the present invention.

Because the human eye is relatively poor at distinguishing between relative intensities, it may be desirable to further equip the measuring means with means for digitizing the output of the camera using, for example, a commercially available microprocessor, such as the Apple Macintosh, IBM AT or compatible microprocessor having suitable hardware and software to permit the intensities within the field of the camera to be filtered, averaged and quantified, such as the JAVA software package from Jandel Scientific, ImagePro from Media Cybernetics or Image from NIH. In addition, digitized output from a camera may be processed, for example, by comparison to a predetermined lookup table (LUT) within the context of the software or the digitized values may be applied to an equation specific to describe the relationship between fluorescence intensity and the concentration level of oxygen present in the bodily fluid or tissue.

As previously discussed, fluorescence intensity is linearly and inversely related to oxygen concentration over a range corresponding to the partial pressure of oxygen in bodily fluid and tissue. This relationship is described by the Stern-Volmer relation. The Stern-Volmer quenching constant or rate constant (k) for the diffusion-controlled collisions between oxygen molecules and probe molecules may be rewritten in terms of the partial pressure of oxygen to better reflect the physiologic processes as indicated in Equation I:

$$F_o/F = 1 + \alpha k_q PO_2 \qquad (I)$$

where $F_o$ is the fluorescence intensity of a fluorescent probe in the absence of oxygen quenching; F is the fluorescence intensity of a fluorescent probe in the presence of oxygen quenching; $\alpha$ is the Bunsen solubility coefficient for oxygen specific to a particular fluid or tissue type; $k_q$ is the quenching constant of the fluorescent probe; and $PO_2$ is the partial pressure of oxygen. If the Bunsen solubility coefficient is not known for a particular tissue or type, it may be determined by performing measurements of the particular tissue or fluid type and preparing calibration lines or curves, as illustrated in Example 2 below. Where the probe comprises pyrenebutyric acid or a salt thereof, the quenching constant ($k_q$) is $1.5 \times 10^{-3}$ per mm Hg $O_2$.

Once the emission light intensity is quantified, the results may be shown graphically, as in FIGS. 1 through 5 or displayed visually by, for example, directing the digitized output to a high-resolution monitor or, for example, digitally coupling fluorescence intensity levels to predetermined colors to provide a pseudo-color image of the various fluorescence intensities.

While not critical to the present invention, depending on the particular equipment used to image the tissue or fluid being examined, it may be desired to provide means to correct any visual aberrations. For example, where the retinal fundus is to be analyzed for oxygen concentration levels according to the prevent invention, corrections which may be determined by one skilled in the art in view of this disclosure should be provided in the hardware or software to correct spatial differences in illumination of the fundus by UV excitation light, as well as possible regional differences in absorption by different regions of the fundus.

The invention will now be illustrated in further detail by reference to the following specific, non-limiting examples.

EXAMPLE 1

Sodium pyrenebutyrate was prepared from pyrenebutyric acid by dissolving 5 grams of pyrenebutyric acid in 350 ml of boiling chloroform and filtering through a Whatman filter paper. 0.7 gram of NaOH in 200 ml of boiling 95% ethanol was added to the hot filtrate and stirred. The resulting solution was kept in the dark and allowed to cool to room temperature. The solution was filtered again and 100 ml of chloroform at room temperature was added to the filtrate. The temperature of the solution was reduced to 0° C. for two hours. Precipitated sodium pyrenebutyrate was reclaimed by filtration, washed twice with cold chloroform and the crystals were dried on a Buchner filter. A sodium pyrenebutyrate solution was then prepared for injection as a 250 mg/ml solution of sodium pyrenebutyrate in DMSO and filtered through a sterile filter with a 0.22 μm pore size to remove bacterial contaminants.

EXAMPLE 2

To observe the affinity of sodium pyrenebutyrate for retinal cells, a living frog retina was sliced from the receptor to vitreal surface and the slice was turned on its side, revealing all of the retinal layers in profile. The slice was incubated in Ringer's solution containing 100 μM sodium pyrenebutyrate and illuminated with UV light at 340 nm (25 nm half-bandwidth). Fluorescence emission was observed at 400–420 nm and the fluorescent image captured on a CCD camera. The output of the camera was digitized using an IBM AT clone microprocessor and the resulting image was stored. The slice was perfused with aerated Ringers at one edge and the 100 μM sodium pyrenebutyrate was found to have no effect on the $PO_2$ profile measured with an oxygen microcathode within the retinal layers.

The retinal slice was bound by glass on the bottom by a perfusion chamber, on the receptor and vitreal surfaces by pieces of microscope slide and at the top by a cover slip. Only the cut left edge of the slice was exposed to oxygen containing perfusate. The cut edge of the slice was perfused with Ringer brought to 0 $PO_2$ by including glucose oxidase in the glucose-containing Ringer. Average intensities were then recorded for the tissue in the absence of oxygen, yielding the values for $F_o$ for each pixel location in the digitized slice image.

To obtain the Bunsen solubility coefficient specific to retinal tissue, the dark current (current in the CCD array in the absence of light stimulation) was first subtracted and the pixel values in the absence of oxygen ($F_o$) were divided pixel-by-pixel by the pixel array for the fluorescent slice in the presence of oxygen (F). The result of this division was then compared to $PO_2$ values obtained by advancing an oxygen microcathode tangentially from the perfused edge to zero $PO_2$ values within each retinal layer. Linear regression between $F_o/F$ and $PO_2$ provides values for $\alpha k_q$ for each retinal layer, as indicated in Table I below, thereby allowing P02 to be derived according to Equation I.

TABLE I

| Retinal Layer | $\alpha k_q$ | Standard Deviation | Coefficient of Determination($R^2$) |
|---|---|---|---|
| OSL | $1.092 \times 10^{-3}$ | $\pm 1.124 \times 10^{-4}$ | 0.8871 |
| ISL | $1.589 \times 10^{-3}$ | $\pm 4.415 \times 10^{-5}$ | 0.9916 |
| ONL | $1.199 \times 10^{-3}$ | $\pm 9.539 \times 10^{-5}$ | 0.9349 |
| OPL | $1.998 \times 10^{-3}$ | $\pm 3.068 \times 10^{-5}$ | 0.9981 |
| INL | $1.035 \times 10^{-3}$ | $\pm 7.557 \times 10^{-5}$ | 0.9352 |
| IPL | $1.125 \times 10^{-3}$ | $\pm 8.099 \times 10^{-5}$ | 0.9415 |
| GCL | $2.176 \times 10^{-3}$ | $\pm 3.716 \times 10^{-5}$ | 0.9979 |

The resulting surface plot of the steady state $PO_2$ along and within the retinal layers is graphically illustrated in FIG. 1, illustrating the decrease of $PO_2$ from the perfused edge as oxygen is consumed within the retinal layers and diffuses between the layers.

The validity of this technique was determined by comparing by linear regression the $PO_2$ values obtained with an oxygen microcathode with the $PO_2$ values derived from the fluorescent probe. A coefficient of determination ($R^2$) of 0.9715 was observed, and the results of this validation are graphically illustrated in FIG. 2. These results indicate that the fluorescent probe of the present invention provides a valid, non-consumptive means of evaluating retinal tissue oxygen levels in space and time.

EXAMPLE 3

Figure 3:
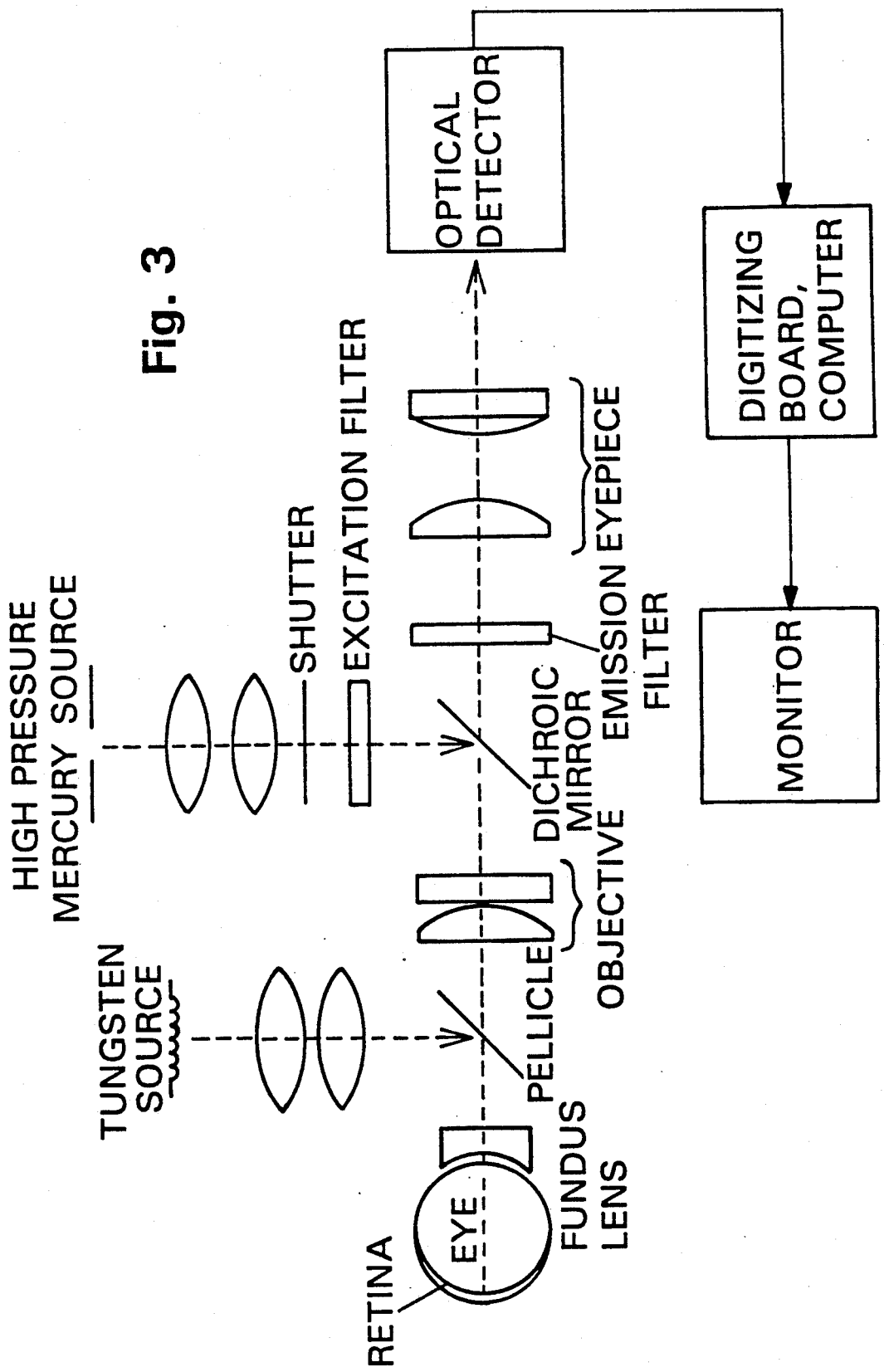
FIG. 3 is a schematic illustration of an imaging apparatus which may be used to perform the methods of the present invention.
Figure 4:
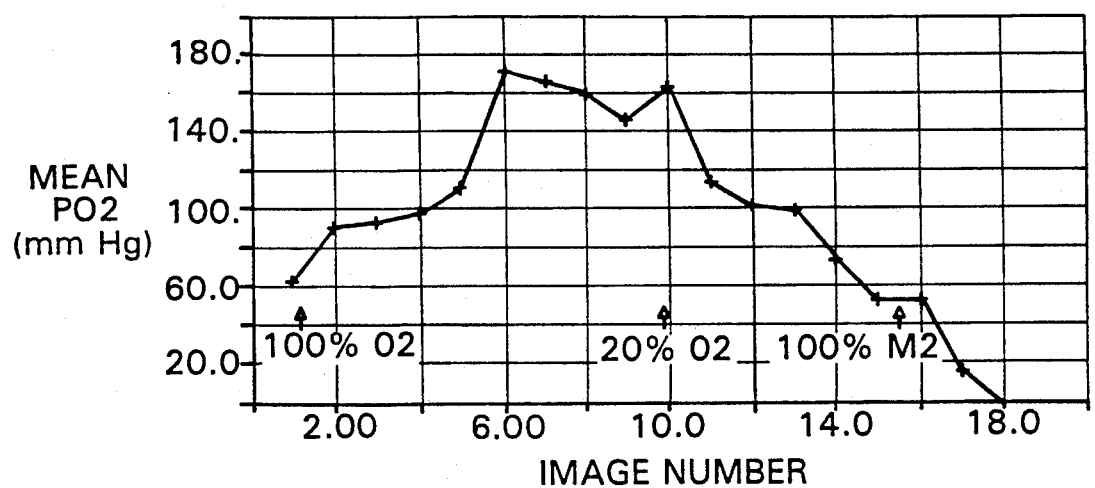
FIG. 4 is a graphical illustration of means $PO_2$ levels in a region of a rat retinal fundus, as measured according to the present invention, when the rat was given different levels of oxygen to breathe.
Figure 5:
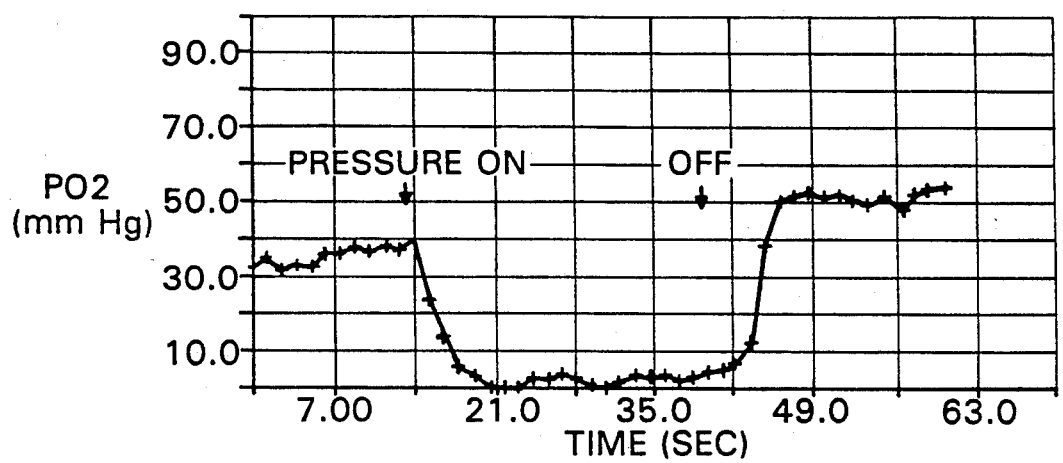
FIG. 5 is a graphical illustration of $PO_2$ in a rat retina, as measured according to the present invention, as a function of increased and relieved intraocular pressure.

To measure the oxygen concentration levels in animal retinal tissue in vivo, an imaging apparatus was set up as follows and schematically illustrated in FIG. 3. The retinal fundus was imaged by a compound microscope using appropriate magnification and corneal refraction was negated using a fundus lens constructed of UV light-transmitting glass. The microscope was modified by the addition of a shuttered epifluorescence system using a high-pressure mercury bulb as a light source, a pellicle within the optical path to permit the retinal fundus to be observed in a bright field visible light using a tungsten light source, an excitation filter (340 nm peak, 25 nm band pass), a dichroic mirror which reflected wavelengths less than 400 nm to the retinal fundus and passed emitted wavelengths greater than 400 nm to a high-gain, low-noise CCD camera fitted to the microscope. The output of the CCD camera was digitized using an IBM AT clone computer, directing the output to a high-resolution RGB monitor. The digitized intensities were converted to relative oxygen concentration.

EXAMPLE 4

A sodium pyrenebutyrate solution prepared in accordance with the method of Example 1 was administered to an albino rat using a single intravenous or intraperitoneal injection at a dosage of 250 mg/kg body weight. Stable concentration levels of the oxygen probe were reached within the retinal tissue after one hour. The rat was anesthetized with intraperitoneal nembutal (50 mg/kg). The pupil was dilated using commercially available mydriatics. A mask was fitted over the animal's nose and mouth and the average $PO_2$ of a region of the rat retinal fundus was determined using the apparatus of Example 3 when the rat was given different levels of oxygen to breathe. The result of this procedure is graphically illustrated in FIG. 4 and demonstrates that the oxygen probe of the present invention provides in vivo measurements of retinal $PO_2$ at different metabolic conditions.

EXAMPLE 5

Following the procedures of Example 4, an albino rat was injected with sodium pyrenebutyrate, anesthetized, and the pupil was dilated. The rat retina was rendered ischemic by rapid (less than one second) increases in intraocular pressure (IOP) capable of blanching the retinal vessels as observed during bright-field examination of the retinal vessels. As graphically illustrated in FIG. 5, subsequent to rapid increase in IOP, the $PO_2$ decreases exponentially towards 0 $PO_2$. With the release of pressure, the $PO_2$ returns exponentially, demonstrating an overshoot similar to that observed in blood flow measurements under similar conditions. This decrease and recovery of oxygen concentration levels in retinal tissue indicate that this procedure may be used to obtain a gross measure of retinal oxygen consumption in diseased states, such as glaucoma.

EXAMPLE 6

Figure 6:
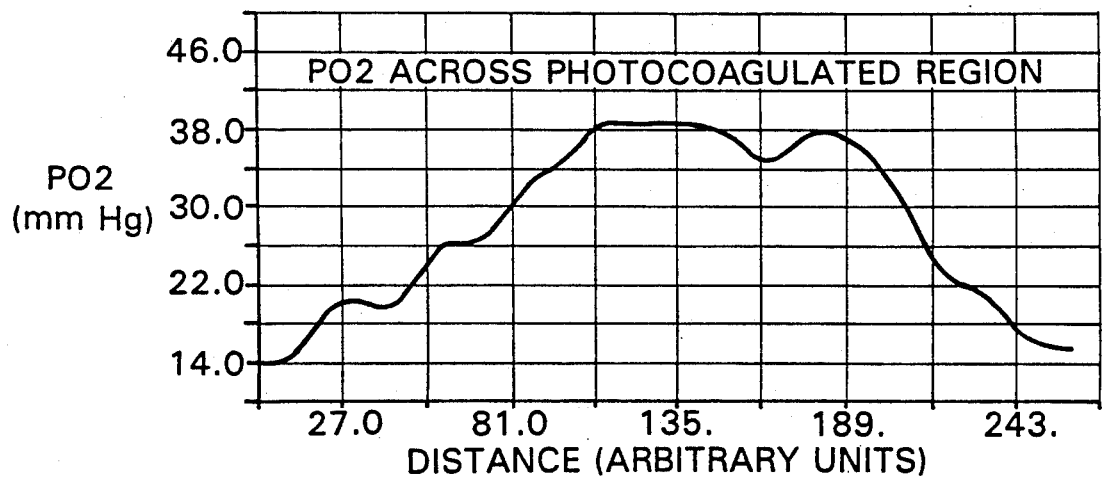
FIG. 6 is a graphical illustration of $PO_2$ levels in a rat retina, measured according to the present invention, as a function of photocoagulation by laser burns over restricted regions of the retina.

To explore the effects of panretinal photocoagulation (PRP) on retinal $PO_2$, a region of an albino rat retina received a number of restricted photocoagulating laser burns (50 μm, 500 mW, 0.5 second duration). Two days after PRP, the rat was subjected to the procedures of Example 4 to measure the $PO_2$ levels across the photocoagulated region. The results are graphically illustrated in FIG. 6 showing the $PO_2$ levels as measured across the photocoagulated region. As illustrated, the $PO_2$ levels increase over the photocoagulated area, indicating that the beneficial effects of PRP on retinal $PO_2$ may be observed directly using the method of the present invention.

From the foregoing description, it may be seen that the present invention provides an in vivo method for directly measuring oxygen concentration levels in an animal bodily fluid or tissue. The method of the present invention may be useful in diagnostic and therapeutic procedures in ophthalmology, cardiology, gastroenterology, pulmonology, oncology and other fields where the knowledge of oxygen concentration levels in living animal bodily fluids and tissues may provide useful information regarding metabolic rate and viability of the particular tissue or fluid. For example, the oxygen concentration levels of burned or otherwise traumatized tissue is indicative of the extent of damage. In addition, the typically increased metabolic rate of tumor cells may be evaluated using the method of the present invention to allow early detection and diagnosis of cancerous tissue in the eye and elsewhere in the body, for example. Another example demonstrating the use of the present invention is to determine the effect of high altitude or gravity (G) stress on eye and other tissue as reflected by oxygen context. The present invention may also be used to determine the effects of systemic or ophthalmic drugs on tissue oxygenation. Still other uses will be appreciated by those skilled in the medical and biological arts in view of this disclosure.

The present invention may be embodied in other specific forms without departing from the spirit or essential attributes thereof and, accordingly, reference should be made to the appended claims, rather than to the foregoing specification as indicating the scope of the invention.

I claim:

1. A method for in vivo measurement of oxygen concentration levels in an animal bodily tissue comprising administering a biocompatible fluorescent probe sensitive to oxygen quenching and having a known unquenched fluorescence intensity to an animal body in an amount sufficient to allow the probe to accumulate in the tissue, exposing the tissue to excitation light, measuring fluorescent emission light intensity form the probe in the tissue and determining the oxygen concentration level of the tissue by comparing the known unquenched fluorescence intensity and the measured fluorescence intensity.

2. The method according to claim 1, wherein the fluorescent probe has a fluorescent lifetime greater than about 70 nsec.

3. The method according to claim 2, wherein the fluorescent probe has a fluorescent lifetime of about 135 nsec.

4. The method according to claim 1, wherein the biocompatible fluorescent probe comprises pyrenebutyric acid or a biocompatible salt form thereof.

5. The method according to claim 4, wherein the fluorescent probe comprises sodium pyrenebutyrate.

6. The method according to claim 1, wherein the fluorescent probe is present in a solution.

7. The method according to claim 6, wherein the solution comprises dimethyl sulfoxide or physiologic saline.

8. The method according to claim 6, wherein the fluorescent probe is present in the solution in an amount of about 250 mg to about 1000 mg per ml of solution.

9. The method according to claim 8, wherein the fluorescent probe is present in the solution in an amount of about 250 mg per ml of solution.

10. The method according to claim 6, wherein the fluorescent probe is administered to the animal body in an amount of about 25 mg to about 250 mg per kg of body weight.

11. The method according to claim 10, wherein the fluorescent probe is administered to the animal body in an amount of about 250 mg per kg of body weight.

12. The method according to claim 6, wherein the fluorescent probe is administered by intravenous or intraperitoneal injection.

13. The method according to claim 6, wherein the fluorescent probe is administered topically.

14. The method according to claim 1, wherein the fluorescent probe is present in means for targeting the probe to a predetermined tissue type in the animal body.

15. The method according to claim 14, wherein the targeting means comprises a liposome.

16. The method according to claim 15, wherein the liposome is a light-sensitive liposome.

17. The method according to claim 1, wherein excitation light is exposed to the tissue using excitation means disposed outside the animal 18. The method according to claim 17, wherein the excitation means produces ultraviolet light.

19. The method according to claim 1, wherein the tissue is exposed to light having wavelengths less than about 400 nm.

20. The method according to claim 1, wherein the oxygen concentration level is determined according to Equation I:

$$F_o/F = 1 + \alpha k_1 PO_2 \qquad (I)$$

where $F_o$ is the fluorescence intensity of a fluorescent probe in the absence of oxygen quenching; F is the fluorescence intensity of a fluorescent probe in the presence of oxygen quenching; $\alpha$ is the Bunsen solubility coefficient for oxygen specific to a particular tissue type; $k_q$ is the quenching constant of the fluorescent probe; and $PO_2$ is the partial pressure of oxygen.

21. The method according to claim 20, wherein $k_q$ is $1.5 \times 10^{-3}$ per mm Hg $O_2$ where the tissue is retinal tissue.

* * * * *